United States Patent [19]
Zhang et al.

[11] Patent Number: 5,922,918
[45] Date of Patent: *Jul. 13, 1999

[54] METHOD FOR MAKING AN OPTICALLY ACTIVE DIPHOSPHINE LIGAND

[75] Inventors: Xiaoyaong Zhang; Noboru Sayo, both of Kanagawa, Japan

[73] Assignee: Takasago International Corporation, Tokyo, Japan

[*] Notice: This patent is subject to a terminal disclaimer.

[21] Appl. No.: 08/957,020

[22] Filed: Oct. 24, 1997

[30] Foreign Application Priority Data

Oct. 24, 1996 [JP] Japan .................................... 8-282157

[51] Int. Cl.$^6$ ....................................................... C07F 9/50
[52] U.S. Cl. ................................................................ 568/17
[58] Field of Search ........................................ 568/517, 17

[56] References Cited

FOREIGN PATENT DOCUMENTS 0 645 696 A1  1/1997  European Pat. Off. .
0 771 812 A1  5/1997  European Pat. Off. .

*Primary Examiner*—Gary Geist
*Assistant Examiner*—Jean F. Vollano
*Attorney, Agent, or Firm*—Sughrue, Mion, Zinn, Macpeak & Seas, PLLC

[57] ABSTRACT

The present invention provides a method for making compound (1) by reacting compound (2) with phosphine oxide (3) in the presence of a transition metal/phosphine complex and optionally reducing the reaction product:

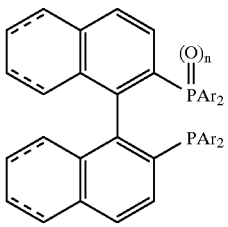

(1)

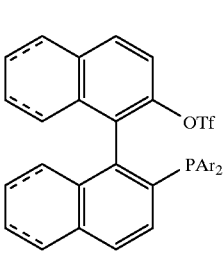

(2)

Ar$_2$P(O)H    (3)

where n represents 0 or 1; the double line having a continuous line and a dotted line represents a double bond or a single bond such that the ring having the double line forms a naphthalene ring or an octahydronaphthalene ring with an adjacent benzene ring; Tf represents a trifluoromethanesulfonyl group; and Ar represents a phenyl group, a substituted phenyl group or a naphthyl group. The present invention provides an economical way to produce compound (1) as a ligand of a complex useful as a catalyst for a variety of asymmetric synthesis reactions.

1 Claim, No Drawings

METHOD FOR MAKING AN OPTICALLY ACTIVE DIPHOSPHINE LIGAND

BACKGROUND OF THE INVENTION

1. Field of the Invention

The present invention relates to a method for making an optically active diphosphine ligand for use in the synthesis of a complex, which in turn is useful as a catalyst for a variety of asymmetric synthesis reactions.

2. Description of the Prior Art

Heretofore, many transition metal complexes have been reported for use in asymmetric synthesis reactions such as asymmetric hydrogenation, asymmetric isomerization and asymmetric hydrosilylation. In particular, many complexes which comprise a transition metal, such as ruthenium, rhodium, iridium or palladium, coordinated with an optically active tertiary phosphine compound, have superior characteristics as a catalyst for asymmetric synthesis reactions. In order to further improve the catalytic performance of these complexes, many phosphine compounds having special structures have been developed (see, for example, "Chemistry of Organometallic Complexes", *Introductory Chemistry* 32, pp. 237–238, Ed. Chemical Society of Japan, 1982 and "Asymmetric Catalysis in Organic Synthesis", R. Noyori, A Wiley-Interscience Publication, 1996).

In particular, 2,2'-bis(diphenylphosphino)-1,1'-binaphthyl (hereinafter referred to as BINAP) is an excellent optically active phosphine. A rhodium complex (Japanese Patent Application Laid-Open (hereinafter referred to as "JP-A") No. 55-61,973) having BINAP as a ligand and a ruthenium complex (JP-A No. 61-6,390) having BINAP as a ligand have been reported. Furthermore, a rhodium complex (JP-A No. 60-199,898) having 2,2'-bis(di(p-tolyl)phosphino)-1,1'-binaphthyl (hereinafter referred to as p-Tol-BINAP) as a ligand and a ruthenium complex (JP-A No. 61-63,690) having the same ligand have each been reported as providing excellent effects in asymmetric hydrogenation and isomerization reactions. Additionally, JP-A No. 4-139,140 discloses a ruthenium complex comprising 2,2'-bis (diphenylphosphino)-5,5',6,6',7,7',8,8'-octahydro-1,1'-binaphthyl (hereinafter referred to as H8-BINAP) as a ligand, and reports that this complex provides an excellent effect in an asymmetric hydrogenation reaction.

An industrial method hitherto known for making the above phosphine compounds consists of the procedure illustrated by the following reaction steps: brominating a racemic binaphthol (7) by means of triphenylphosphine dibromide at a high temperature (240 to 320° C.) to prepare compound (8), forming a Grignard reagent (9) from the compound (8), condensing the Grignard reagent (9) with a diarylphosphinyl chloride to produce a phosphine dioxide (10), optical resolving the phosphine dioxide (10) to prepare compound (11), and reducing compound (11) by means of a reducing agent such as trichlorosilane to a tertiary phosphine compound (a type of BINAP compound) (1b) (H. Takaya, K. Mashima, K. Koyano, M. Yagi, H. Kumobayashi, T. Taketomi, S. Akutagawa, and R. Noyori, *J. Org. Chem.*, 1986, Vol. 51, pp. 629).

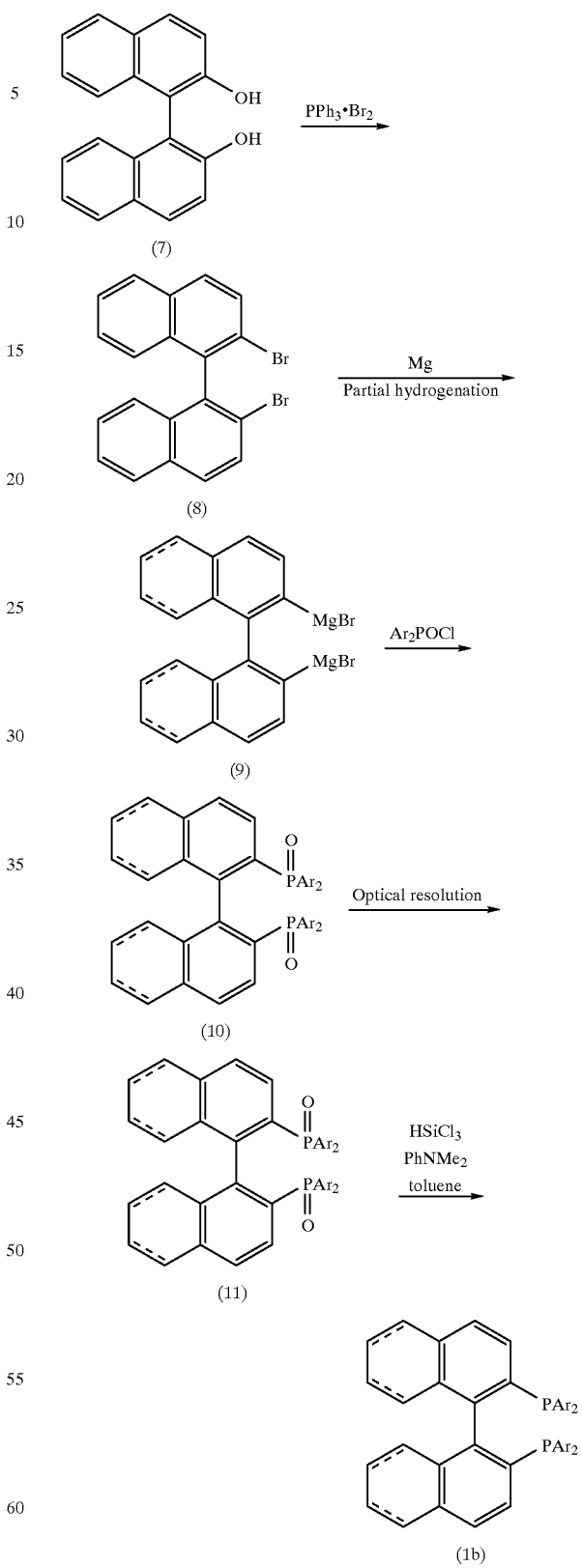

where the double line having a continuous line and a dotted line represents a double bond or a single bond such that the ring having the double line forms a naphthalene ring or an octahydronaphthalene ring with an adjacent benzene ring;

and Ar represents a phenyl group, a substituted phenyl group (having 1 to 3 substituent groups, which may be the same or different, selected from the group consisting of a halogen atom, a lower alkyl group, a lower alkoxy group and a halogenated lower alkyl group) or a naphthyl group which may have a lower alkyl or lower alkoxy substituent.

Another method comprises hydrogenating binaphthyl bromide to prepare 5,5',6,6',7,7',8,8'-octahydrobinaphthyl bromide, forming a Grignard reagent from the octahydro-binaphthyl bromide, condensing the Grignard reagent with a diarylphosphinyl chloride to produce a phosphine dioxide, optical resolving the phosphine dioxide, and reducing the resulting compounds by means of a reducing agent such as trichlorosilane to a tertiary phosphine compound (H8-BINAP) (X. Zhang, K. Mashima, K. Koyano, N. Sayo, H. Kumobayashi, S. Akutagawa, and H. Takaya, *J. Chem. Soc. Perkin Trans.* 1, 1994, p.2309). Yet another method comprises preparing 2,2'-bis(trifluoromethanesulfonyloxy)-1,1'-binaphthyl by using an optically active binaphthol and reacting the 2,2'-bis(trifluoromethanesulfonyloxy)-1,1'-binaphthyl with diphenylphosphine in the presence of a nickel/phosphine complex to obtain BINAP (Dongwei Cai, Joseph F. Pyyack, Dean R. Bender, David L. Hughes, Thomas R. Verhoeven, and Paul J. Reider, *J. Org. Chem.*, 1994, Vol. 59, p. 7180).

However, each of above described methods for making an optically active phosphine compound has a problem. For example, in the method of Takaya et al., the reaction vessel is limited, because a high temperature is necessary for brominating binaphthol and because hydrobromic acid is generated in this step. Furthermore, the method by Takaya et al. and the method by Zhang et al. are disadvantageous in that a high temperature and a high hydrogen pressure are also necessary in the hydrogenation reaction of binaphthyl bromide. Also, these methods are uneconomical if only one of the enantiomers is needed, because these methods require optical resolution of the racemic reaction product. In addition, there are many racemic reaction products whose optical resolution is difficult. Besides, the method by Dongwei et al. presents a problem in that diphenylphosphine, which is used in the reaction of this method, is undesirably used in a large amount in industry due to its insufficient stability (diphenylphosphine is readily oxidized) and toxicity. However, this method does not require optical resolution.

SUMMARY OF THE INVENTION

After completing studies to solve the above-described problems of the prior art, the present inventors achieved the invention described herein based on the discovery that the reaction between 2-trifluoromethanesulfonyl-2'-diarylphosphino-5,5',6,6',7,7',8,8'-octahydro-1,1'-binaphthyl or 2-trifluoromethanesulfonyl-2'-diarylphosphino-1,1'-binapthyl with a disubstituted phosphine oxide in the presence of a transition metal/phosphine complex easily leads to the formation of 2-diarylphosphino-2'-diarylphosphinyl-5,5',6,6',7,7',8,8'-octahydro-1,1'-binaphthyl or 2-diarylphosphino-2'-diarylphosphinyl-1,1'-binaphthyl, which can be easily made into a H8-BINAP or BINAP derivative by reduction.

The present invention can be illustrated by the following reactions.

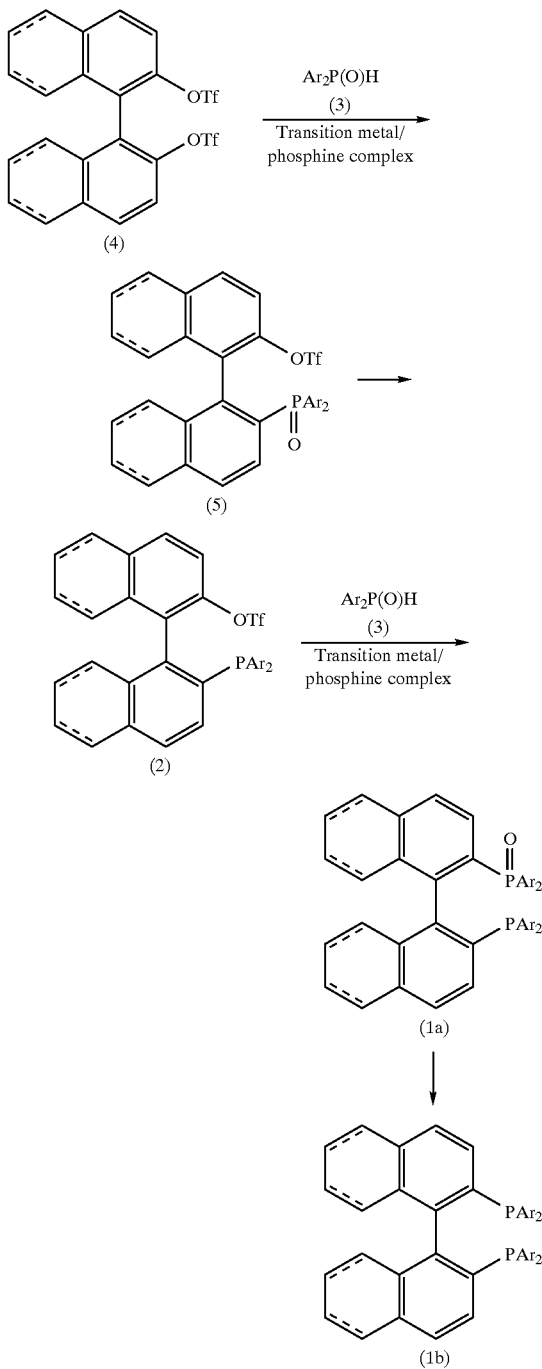

where Tf represents a trifluoromethanesulfonyl group; and the double line having a continuous line and a dotted line and Ar having the same meanings as described above.

That is, the method of the present invention comprises the following procedure: reacting 2,2'-bis(trifluoromethanesulfonyloxy)-1,1'-binaphthyl or 2,2'-bis(trifluoromethanesulfonyloxy)-1,1'-octahydrobinaphthyl represented by general formula (4) and a phosphine oxide represented by general formula (3) in the presence of a transition metal/phosphine complex to form 2-trifluoromethanesulfonyloxy-2'-diarylphosphinyl-1,1'-binaphthyl or 2-trifluoromethanesulfonyloxy-2'-diarylphosphinyl-1,1'-octahydrobinaphthyl represented by general formula (5); reducing the product of the preceding reaction to prepare 2-trifluoromethanesulfonyloxy-2'-diarylphosphino-1,1'-binaphthyl or 2-trifluoromethanesulfonyloxy-2'-diarylphosphino-1,1'-octahydrobinaphthyl represented by general formula (2); reacting the product of the preceding reaction and a phosphine oxide represented by general formula (3) in the presence of a transition metal/phosphine complex to form a compound represented by general formula (1a); and optionally reducing the product of the preceding step to prepare a compound represented by general formula (1b).

PREFERRED EMBODIMENTS OF THE INVENTION

The compound, which is used as a starting material in the present invention and which is represented by general formula (4), can be made, for example, by the following reactions.

In the aforementioned formulae illustrating the method of the present invention, examples of Ar include a substituted phenyl group having 1 to 3 substituents selected from the group consisting of a halogen atom, a lower alkyl group, a lower alkoxy group and a halogenated lower alkyl group. Examples of the halogen atom include fluorine, chlorine, bromine and iodine atoms. Examples of the lower alkyl group include straight or branched alkyl groups having from 1 to 5 carbon atoms. Examples of the lower alkoxy group include straight or branched alkoxy groups having from 1 to 5 carbon atoms. Examples of the halogenated lower alkyl group include straight or branched halogenated alkyl groups having from 1 to 5 carbon atoms.

Examples of the substituted phenyl group include p-tolyl, p-methoxyphenyl, p-dimethylaminophenyl, p-t-butylphenyl, 3,5-dimethylphenyl, 3,5-dimethyl-4-methoxyphenyl, 3,4,5-trimethylphenyl, 3,5-di-t-butylphenyl, 3,4-methylenedioxyphenyl, 3,5-dimethoxylphenyl, 3,4,5-trimethoxylphenyl,

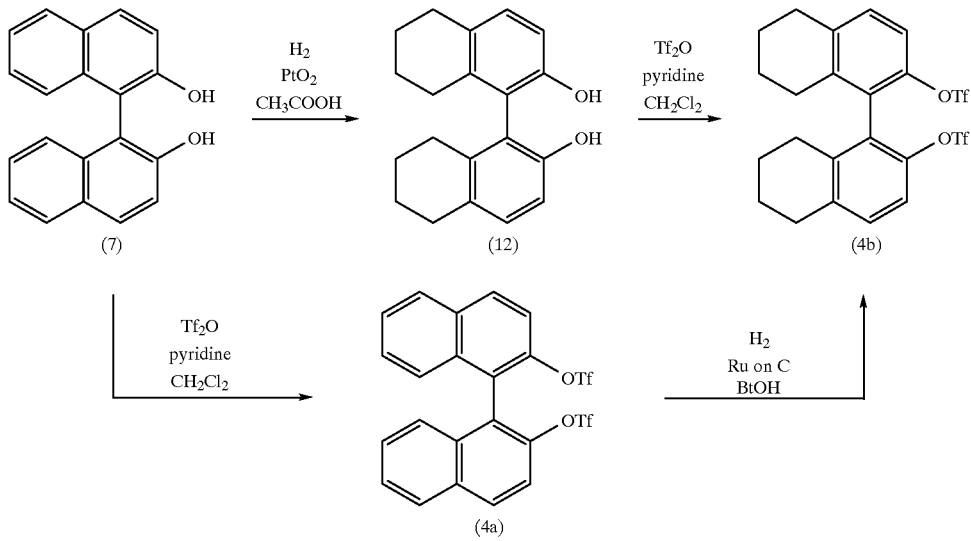

where Tf represents a trifluoromethanesulfonyl group. That is, the compound (4b) can be obtained by a process comprising the steps of hydrogenating optically active binaphthol (7) as a starting material in the presence of a catalytic amount of platinum dioxide to prepare 5,5',6,6',7,7',8,8'-octahydro-2,2'-binaphthol (12), for example, by the method described in D. J. Cram, R. C. Helgeson, S. C. Peacock, L. J. Kaplan, L. A. Domeier, P. Moreau, K. Koga, J. M. Mayer, Y. Chao, M. G. Siegel, D. H. Hoffman, G. D. Y. Sogah, *J. Org. Chem.*, 1978, Vol. 43, p. 1930, and making the product of the preceding step into a ditrifluoromethanesulfonylated compound, for example, by the method described in M. Vondenhof and J. Mattay, *Tetrahedron Lett.*, Vol. 31, pp. 985–988, 1990 and L. Kurz, G. Lee, D. Morgans Jr., M. J. Waldyke, and T. Ward, *Tetrahedron Lett.*, Vol. 31, pp. 6321–6324, 1990 and the method described in Y. Uozumi, A. Tanahashi, S. Y. Lee, and T. Hayashi, *J. Org. Chem.*, 1993, Vol. 58, pp. 1945–1948. Meanwhile, the compound (4a) can be obtained by making the binaphthol (7) into a ditrifluoromethanesulfonylated compound by a similar method. The compound (4b) can also be obtained by hydrogenating the compound (4a) using Ru/C as a catalyst in a solvent such as ethanol, methanol, propanol, isopropanol, tetrahydrofuran, 1,4-dioxane, ethyl acetate or a mixture thereof.

p-chlorophenyl, 3,5-dichlorophenyl, p-fluorophenyl and p-trifluoromethylphenyl groups.

Examples of the naphthyl group include α-naphthyl and β-naphthyl groups. The naphthyl group may have a substituent selected from straight or branched lower alkyl groups having from 1 to 5 carbon atoms and straight or branched lower alkoxy groups having from 1 to 5 carbon atoms. Examples of the substituted naphthyl group include 6-methoxy-β-naphthyl and 6-methoxy-α-naphthyl groups.

In the present invention, the reaction for preparing compound (5) from compound (4) and the reaction for preparing compound (1a) from compound (2) can be effected under nearly the same conditions. The amount of the disubstituted phosphine oxide (3) used in these reactions is generally from 1 to 3 times the molar equivalent of compound (4) or (2), preferably 1 to 1.5 times its molar equivalent. Preferably, the disubstituted phosphine oxide (3) for use in the present invention is purified by means of recrystallization or silica gel chromatography. The disubstituted phosphine oxide (3) can be synthesized by a procedure which comprises making ArCl, ArBr or ArI into a Grignard reagent, and reacting the Grignard reagent with diethyl phosphite according to the method of B. B. Hunt and B. C. Saudwers et al. as described in *J. Chem. Soc.*, 1957, p. 2413 or the method of H. R. Hays et al. as described in *J. Org. Chem.*, 1968, Vol. 33, p. 3690.

Examples of the transition metal/phosphine complex include complexes of transition metals such as copper, iron, cobalt, nickel and palladium. More specifically, examples thereof include the following compounds. In the following examples, Me stands for methyl, Ph stands for phenyl, dppe stands for 1,2-bisdiphenylphosphinoethane, dppp stands for 1,3-bisdiphenylphosphinopropane and dppb stands for 1,4-bisdiphenylphosphinobutane.

Cu: $CuMe(PPh_3)_3$, $(CuMe)_2(dppe)$, $CuCl(PPh_3)_3$

Fe: $Fe(CO)_2(PPh_3)_3$, $FeCl_2(PPh_3)$, $FeCl_2(dppe)$, $FeHCl(dppe)$, $FeCl_3(PPh_3)_3$, $FeCl_2(dppp)$, $FeCl_2(dppb)$ Co: $CoCl(PPh_3)_3$, $CoCl_2(dppe)$, $CoCl_2(dppp)$, $CoCl_2(dppb)$ Ni: $Ni(PPh_3)_4$, $Ni(PPh_3)_2$, $NiCl_2(dppe)$, $NiCl_2(dppp)$, $NiCl_2(dppb)$ Pd: $PdCl_2(PPh_3)_2$, $PdCl_2(dppe)$, $PdCl_2(dppp)$, $PdCl_2(dppb)$ The transition metal/phosphine complex is used in a catalytic amount, and is preferably in the range of from 5 to 20 mol % based on the amount of compound (4) or (2).

In order to neutralize the trifluoromethanesulfonyloxy group which splits off at the time of the reaction, a base is preferably present in the reaction system. Examples of the base include 1,4-diazabicylco[2.2.2]octane (DABCO), diazabicycloundecene (DBU), tetramethylethylenediamine (TMEDA), dimethylaniline, 1,4-dimethylpiperazine, 1-methylpiperidine, 1-methylpyrrolidine, quinuclidine, 1-methylmorpholine, triethylamine, diisopropylethylamine and 1-methyl-2,2,6,6-tetramethylpiperidine.

Usually, the reaction is effected in a solvent. Examples of the solvent include N,N-dimethylformamide (DMF), dimethyl sulfoxide (DMSO), N-methylpyrrolidone (NMP) and dimethylacetamide (DMA). Generally, the reaction temperature is in the range of from 80 to 140° C., preferably in the range of from 100 to 120° C.

The reaction for preparing compound (2) from compound (5) and the reaction for preparing compound (1b) from compound (1a) are effected using a conventional reducing means, for example, trichlorosilane as a reducing agent.

More specifically, the reduction reactions in the present invention can utilize benzene, toluene or xylene as a solvent, triethylamine, diisopropylethylamine, dimethylaniline or diethylaniline as a base, trichlorosilane as a reducing agent and a reaction temperature in the range of from 80 to 130° C.

Compounds (1a) and (1b) prepared in the above described method of the present invention each is useful as a ligand for forming a complex with a transition metal. The compounds (1a) and (1b) can jointly by represented by the following formula (1).

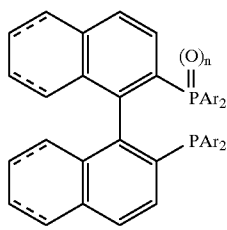

(1)

where n represents 0 or 1 and Ar has the same meaning as given above.

The complex of the present invention, which comprises compound (1) and a transition metal, is useful as a catalyst for an asymmetric synthesis reaction.

The present invention provides an economical method for preparing H8-BINAP and BINAP derivatives using optically active binaphthol as a starting material. In addition, a complex of a transition metal with a H8-BINAP or BINAP derivative can be used as a catalyst in an asymmetric synthesis reaction, for example, an asymmetric hydrogenation reaction or an asymmetric hydrosilylation reaction, to provide the target product at high yield and at a high rate of excess enantiomer. Furthermore, a reaction product having a desirable absolute configuration can be obtained in the asymmetric synthesis reaction by using a transition metal complex as a catalyst with a ligand which is either a (−) enantiomer or a (+) enantiomer of the compound of the present invention.

EXAMPLES

In order that those skilled in the art will be better able to practice the present invention, the following Examples are given by way of illustration and not by way of limitation. The measurements in the following Examples were conducted using the following apparatus.

Nuclear Magnetic Resonance $^1$H NMR AM400 (400 MHz) (manufactured by Bruker Co., Ltd.)

$^{31}$p NMR AM400 (162 MHz) (manufactured by Bruker Co., Ltd.)

Melting Point

MP-500D (manufactured by Yanaco Co., Ltd.)

Optical Rotation

DIP-4 (manufactured by Nihon Bunkoh Co., Ltd.)

Gas Chromatography (GLC)

5890-II (manufactured by Hewlett Packard Co., Ltd.)

High-performance Liquid chromatography(HPLC)

LC10AT & SPD10A (manufactured by Shimadzu Corporation)

Mass Spectrometry(MASS)

M-80B (manufactured by Hitachi Ltd.)

Example 1

Synthesis of (R)-2,2'-dihydroxy-5,5',6,6',7,7',8,8'-octahydro-1,1'-binaphthyl (R)-binaphthol (3.0 g, 10.5 mmol), 15% platinum dioxide (360 mg) and 75 ml of acetic acid were placed in a 200 ml autoclave, and the contents were stirred for 18 hours at a hydrogen gas pressure of 3 atm and at 5° C. The contents were further stirred for 7 days at a hydrogen gas pressure of 10 atm and at 18° C. The reaction mixture was then filtered through celite and washed with ethyl acetate. After the filtrate was washed with water, the organic layer was washed with a saturated $NaHCO_3$ solution. The aqueous layer was extracted with ethyl acetate, and the organic layers were combined into a single organic solution. After drying the organic solution with anhydrous magnesium sulfate, the solvent was removed by distilling at reduced pressure to obtain 3.03 g (yield: 98.1%) of the above captioned compound as white crystals.

mp: 167 to 169° C.

$[\alpha]_D^{25}$: +48.9° (c 1.10, $CHCl_3$)

$^1$H-NMR($CDCl_3$)δ: 1.53–1.76(m,8H), 2.16(dt, J=17.1, 6.4 Hz, 2H), 2.29(dt, J=17.5, 6.3 Hz, 2H), 4.54(s, 2H), 6.83(d, J=8.3 Hz, 2H), 7.07(d, J=8.3 Hz, 2H)

Mass spectrum: m/z 294($M^+$)

Example 2

Synthesis of (R)-2,2'-ditrifluoromethanesulfonyloxy-5,5',6,6',7,7',8,8'-octahydro-1,1'-binaphthyl (R)-2,2'-dihydroxy-5,5',6,6',7,7',8,8'-octahydro-1,1'-binaphthyl (18.17 g, 61.72 mmol) and pyridine (12.5 ml, 154 mmol) were dissolved in methylene chloride (90 ml) and the solution was cooled to 0° C. Then, trifluoromethanesulfonic anhydride (38.35 g, 135.9 mmol) was added dropwise to the solution, and the solution was stirred for 20 hours at room temperature. The reaction mixture was then admixed with 2N hydrochloric acid (100 ml) and washed. The organic layer was washed three times with water (100 ml) and a sodium chloride aqueous solution (100 ml) in that order. Then, the solvent was removed by distilling at reduced pressure to obtain 36.56 g of residue as a crude product. The crude product was dissolved in hexane and recrystallized to obtain 32.82 g (95% yield) of the above captioned product.

Example 3

Synthesis of (R)-2-diphenylphosphinyl-2'-trifluoromethanesulfonyloxy-5,5',6,6',7,7',8,8'-octahydro-1,1'-binaphthyl (R)-2,2'-ditrifluoromethanesulfonyloxy-5,5',6,6',7,7',8,8'-octahydro-1,1'-binaphthyl (3.0 g, 5.4 mmol), palladium acetate (121 mg, 0.54 mol) and 1,3-bis(diphenylphosphino)propane (222 mg, 0.54 mmol) were dissolved in DMSO (25 ml). The solution was stirred for 1.5 hours at room temperature. The solution was admixed with a solution made by dissolving diphenylphosphine oxide (1.41 g, 7.0 mmol) and diisopropylethylamine (1.04 g, 8.1 mmol) in DMSO (15 ml). The resulting solution was stirred for 6 hours at 100° C. After concentrating, the solution was admixed with methylene chloride (40 ml) and 1N hydrochloric acid (20 ml). The solution was then stirred for 30 minutes at room temperature. Next, the solution was separated into layers, and the aqueous layer was extracted with methylene chloride. The organic layers were combined into a single solution, and the solution was washed with water. After drying with anhydrous magnesium sulfate, the solution was concentrated. The solution was then purified by silica gel column chromatography (hexane: ethyl acetate=4:1 to 1:1 by volume) to obtain 2.13 g (yield: 65%) of the above captioned compound as yellowish while crystals.

mp: 148 to 150° C.

$[\alpha]_D^{24}$: −3.35° (c 1.00, toluene)

$^{31}$P-NMR(CDCl$_3$)δ: 28.12(s)

EI-Mass spectrum: m/z 610(M$^+$)

Example 4

Synthesis of (R)-2-diphenylphosphino-2'-trifluoromethanesulfonyloxy-5,5',6,6',7,7',8,8'-octahydro-1,1'-binaphthyl Trichlorosilane (2.1 ml, 21 mmol) was added to a mixture of (R)-2-diphenylphosphinyl-2'-trifluoromethanesulfonyloxy-5,5',6,6',7,7',8,8'-octahydro-1,1'-binaphthyl (2.10 g, 3.44 mmol), toluene (30 ml) and dimethylaniline (2.50 g, 20.6 mol). The solution was stirred at 90° C. for 1 hour and then heated at reflux for 15 hours. After cooling the reaction mixture, 15% NaOH solution (30 ml) was gradually added thereto. The aqueous layer was extracted twice with 10 ml of toluene and the organic layers were combined into a single solution. The organic solution was washed with water twice (10 ml), 1N hydrochloric acid (30 ml) and water (20 ml) in that order, followed by concentrating the organic layer. Then, the organic solution was purified by silica gel column chromatography (hexane:ethyl acetate=9:0 to 9:1 by volume) to obtain 1.82 g (yield: 89%) of the above captioned compound as a yellow solid.

$^{31}$P-NMR(CDCl$_3$)δ: −13.72(s)

CI-Mass spectrum m/z: 595 (M$^+$+H)

Example 5

Synthesis of (R)-2-diphenylphosphino-2'-diphenylphosphinyl-5,5',6,6',7,7',8,8'-octahydro-1,1'-binaphthyl Under a nitrogen gas stream, a mixture of (R)-2-diphenylphosphino-2'-trifluoromethanesulfonyloxy-5,5',6,6',7,7',8,8'-octahydro-1,1'-binaphthyl (602 mg, 1.01 mmol), Ni(dppe)Cl$_2$ (30 mg, 0.058 mmol), DABCO (227 mg, 2.03 mmol) and DMF (5 ml) was stirred for 15 minutes at room temperature. The solution was then admixed with diphenylphosphine oxide (381 mg, 1.88 mmol) as a solution in DMF (5 ml). Then, the solution was stirred for 24 hours at 100° C. After the solvent was removed by distilling at reduced pressure, the residual product was dissolved in dichloromethane (10 ml). The organic layer was washed with water (5 ml), 2N hydrochloric acid (4 ml) and water (5 ml) in that order, and the solution was dried using anhydrous sodium sulfate. After removing the solvent by distilling at reduced pressure, the residue was purified by silica gel column chromatography (hexane:ethyl acetate=20:1 to 5:1 by volume) to obtain 0.21 g (yield: 32%) of (R)-2,2'-bis(diphenylphosphino)-5,5',6,6',7,7',8,8'-octahydro-1,1'-binaphthyl (H8-BINAP) and 0.31 g (yield: 47%) of (R)-2-diphenylphosphino-2'-diphenylphosphinyl-5,5',6,6',7,7',8,8'-octahydro-1,1'-binaphthyl.

mp: 224 to 226° C.

$[\alpha]_D^{25}$: +91.59° (c 0.516, toluene)

$^{31}$P-NMR(CDCl$_3$)δ: −16.37(s), 28.29(s)

$^1$H-NMR(CDCl$_3$)δ: 0.61–0.73(m, 1H), 0.99–1.16(m, 2H), 1.18–1.48(m, 6H), 1.59–1.81(m, 3H), 2.52–2.68(m, 4H), 6.88(d, J=7.9 Hz, 1H), 6.92–6.98(m, 2H), 7.01–7.12(m, 4H), 7.13–7.58(m,13H), 7.48–7.62(m,4H)

EI-Mass spectrum: m/z 646(M$^+$)

Example 6

Synthesis of (R)-2,2'-bis(diphenylphosphino)-5,5',6,6',7,7',8,8'-octahydro-1,1'-binaphthyl Trichlorosilane (0.38 g, 2.8 mmol) was added to a mixture of (R)-2-diphenylphosphinyl-2'-trifluoromethanesulfonyloxy-5,5',6,6',7,7',8,8'-octahydro-1,1'-binaphthyl (0.3 g, 0.46 mmol), toluene (5 ml) and dimethylaniline (0.34 g, 2.8 mmol). The solution was heated at reflux for 21 hours. After cooling the reaction mixture, 3N NaOH solution (5 ml) was gradually added dropwise thereto. The aqueous layer was extracted twice with 5 ml of toluene, and the organic layers were combined into a single solution. The organic solution was washed with water (5 ml) twice, 1N hydrochloric acid (5 ml) and water (5 ml) twice in that order, followed by concentrating the organic layer. Then, the organic solution was purified by silica gel column chromatography (hexane:ethyl acetate=1:0 to 9:1 by volume) to obtain 0.27 g (yield: 43%) of the above captioned compound as yellow crystals.

mp: 206 to 208° C.
[α]$_D^{24}$: +71.9° (c 0.50, toluene)
$^{31}$P-NMR(CDCl$_3$)δ: −15.31(s)
EI-Mass spectrum: m/z 630(M$^+$)

Example 7

Synthesis of (S)-2,2'-bis(trifluoromethanesulfonyloxy)-1,1'-binaphthyl (S)-binaphthol (36.2 g, 127 mmol) and pyridine (25.2 g, 319 mmol) were dissolved in methylene chloride (181 ml), and the solution was cooled down to 0° C. Trifluoromethanesulfonic anhydride (76.5 mg, 271 mmol) was added dropwise to the solution. Then, the solution was stirred for 18 hours at room temperature. The solution was then admixed with 2N hydrochloric acid (200 ml) and washed. The organic layer was washed with water and aqueous sodium chloride solution in that order, and the solvent was removed by distilling at reduced pressure to obtain 69.3 g of a crude product. The crude product was purified by recrystallizing from hexane (280 ml) to obtain 64.1 g (yield: 92%) of the above captioned compound.
$^1$H-NMR(CDCl$_3$)δ ppm: 7.25–8.15(m, ArH)

Example 8

Synthesis of (S)-2,2'-ditrifluoromethanesulfonyloxy-5,5',6,6',7,7',8,8'-octahydro-1,1'-binaphthyl (S)-2,2'-bis(trifluoromethanesulfonyloxy)-1,1'-binaphthyl (1.1 g, 2 mmol), 5% Ru/C (0.1 g) and 95% EtOH (10 ml) were placed in an autoclave, and the contents were stirred for 8 hours at a hydrogen gas pressure of 50 atm and at a reaction temperature of 120° C. Upon completion of the reaction, the catalyst was removed by filtration, and the filtrate was concentrated to obtain 1.1 g(yield: 98%) of the above captioned compound.

Example 9

Synthesis of (R)-2-diphenylphosphinyl-2'-trifluoromethanesulfonyloxy-1,1'-binaphthyl (R)-2,2'-bis(trifluoromethanesulfonyloxy)-1,1'-binaphthyl (11 g, 20 mmol), palladium acetate (0.225 g, 50 mol %) and 1,4-bis(diphenylphosphino)propane (0.43 g, 50 mol %) were dissolved in DMSO (100 ml), and the resulting solution was stirred for 1.5 hours at room temperature. The solution was admixed with a solution made by dissolving diphenylphosphine oxide (8.08 g, 40 mmol) and diisopropylethylamine (20 ml) in DMSO (100 ml). The resulting solution was stirred for 12 hours at 100° C. After cooling to room temperature, the solution was admixed with methylene chloride (75 ml). To the solution, which was cooled in an ice/water bath, 2N hydrochloric acid (100 ml) was gradually added dropwise thereto. The solution was then stirred for 30 minutes at room temperature. Then, the solution was separated into layers, and the aqueous layer was extracted with methylene chloride. The organic layers were combined into a single solution, and the solution was washed with water. After drying with anhydrous magnesium sulfate, the organic solution was concentrated. The solution was then purified by silica gel column chromatography (hexane:ethyl acetate=4:1 to 1:4 by volume) to obtain 11.5 g (yield: 96%) of the above captioned compound as yellowish white crystals.
[α]$_D^{24}$: +44.45° (c 0.50, CHCl$_3$)
$^1$H-NMR(CDCl$_3$)δ: 7.0–8.01(m, ArH)
$^{31}$P-NMR(CDCl$_3$)δ: 28.73

Example 10

Synthesis of (R)-2-diphenylphosphino-2'-(trifluoromethanesulfonyloxy)-1,1'-binaphthyl Trichlorosilane (2.5 ml, 25 mmol) was added to a mixture of (R)-2-diphenylphosphinyl-2'-(trifluoromethanesulfonyloxy)-1,1'-binaphthyl (11.5 g, 19.2 mmol), toluene (170 mmol) and dimethylaniline (3.1 ml, 24 mmol). The resulting reaction mixture was stirred for 1 hour at 90° C. and thereafter heated at reflux for 7 hours. Then, the reaction mixture was cooled and 1N NaOH solution (150 ml) was gradually added dropwise to the reaction mixture. The aqueous layer was extracted with toluene (50 ml). The organic layers were combined into a single solution, which was washed twice with water (150 ml), 1N hydrochloric acid (150 ml) and water (150 ml) in that order. After concentrating, the organic solution was then purified by silica gel column chromatography (hexane:ethyl acetate=1:0 to 9:1 by volume) to obtain 9.03 g (yield: 80%) of the above captioned compound as a yellow solid.
mp: 55 to 58° C.
[α]$_D^{24}$: −110.6° (c 0.85, CH$_2$Cl$_2$)
$^1$H-NMR(CDCl$_3$)δ: 6.63–8.2(m, ArH)
$^{31}$P-NMR(CDCl$_3$)δ: 30.80

Example 11

Synthesis of (R)-2-diphenylphosphino-2'-diphenylphosphinyl-1,1'-binaphthyl

Under a nitrogen gas stream, a mixture of (R)-2-diphenylphosphino-2'-trifluoromethanesulfonyloxy-1,1'-binaphthyl (0.99 g, 1.63 mmol), Ni(dppe)Cl$_2$ (179.4 mg, 0.340 mmol), DABCO (875.0 mg, 7.02 mmol) and DMF (4 ml) was stirred for 1 hour at room temperature. The solution was then admixed with diphenylphosphine oxide (0.49 g, 2.4 mmol) as a solution in DMF (2 ml). Then, the solution was stirred for 25 hours at 100° C. After the solvent was removed by distilling at reduced pressure, the residue was dissolved in dichloromethane (50 ml). The organic layer was washed with water (20 ml) and 1N hydrochloric acid (20 ml), and the organic solution was dried using anhydrous sodium sulfate. After the solvent was removed by distilling at reduced pressure, the residue was purified by silica gel column chromatography (hexane:ethyl acetate=15:1 by volume) to obtain 0.38 g (yield: 37%) of the above captioned compound.
mp: 236 to 238° C.
[α]$_D^{25}$: +97.5° (c 0.82, CHCl$_3$)
$^{31}$P-NMR(CDCl$_3$)δ: −14.55(s), 27.74(s)
$^1$H-NMR(CDCl$_3$)δ: 6.65–7.91(m)
CI-Mass spectrum m/z: 639(M$^+$+H)

Example 12

Synthesis of (R)-2,2'-bis(diphenylphosphino)-1,1'-binaphthyl

Trichlorosilane (0.95 ml, 9.4 mmol) was added to a mixture of (R)-2-diphenylphosphino-2'-diphenylphosphinyl-1,1'-binaphthyl (1.5 g, 2.35 mmol), dimethylaniline (4.8 ml, 4.4 mmol) and toluene (11 ml). The resulting reaction mixture was stirred for 1 hour at 90° C. and thereafter heated at reflux for 16 hours. The reaction mixture was cooled in an ice/water bath, and 3N NaOH solution (20 ml) was added to the reaction mixture. The aqueous layer was extracted with toluene and the organic layer was washed with water (10 ml), 1N hydrochloric acid (20 ml) and water (10 ml) in that order, followed by concentrating the organic solution. Then, the organic solution was purified by silica gel column chromatography (hexane:ethyl acetate=1:0 to 1:1 by volume) to obtain 1.34 g (yield: 92%) of the above captioned compound as a white solid.

mp: 241 to 242° C.
$[\alpha]_D^{24}$: −228° (c 0.679, benzene)
$^{31}$P-NMR(CDCl$_3$)δ: −12.8(s)
CI-Mass spectrum m/z: 622(M$^+$)

Example 13

Synthesis of (S)-2-di(2-naphthyl)phosphinyl-2'-(trifluoromethanesulfonyloxy)-1,1'-binaphthyl (S)-2,2'-bis(trifluoromethanesulfonyloxy)-1,1'-binaphthyl (9.10 g, 16.5 mmol), palladium acetate (0.372 g, 1.65 mmol), 1,3-bis(diphenylphosphino)propane (0.683 g, 1.65 mmol) and sodium formate (0.113 g, 1.65 mmol) were dissolved in DMSO (45 ml), and the resulting solution was stirred for 1.5 hours at room temperature. The solution was admixed with a solution made by dissolving di(2-naphthyl)phosphine oxide (6.00 g, 19.8 mmol) and diisopropylethylamine (5.8 ml, 33 mmol) in DMSO (55 ml). The resulting solution was stirred for 4 hours at 100° C. After cooling to room temperature, the reaction mixture was admixed with methylene chloride (75 ml). To the resulting solution, which was cooled in an ice/water bath, 2N hydrochloric acid (100 ml) was gradually added dropwise. The solution was then stirred for 30 minutes at room temperature. Then, the solution was separated into layers, and the aqueous layer was extracted with methylene chloride. The organic layers were combined into a single solution, and the solution was washed with water. After drying with anhydrous magnesium sulfate, the organic solution was concentrated. The solution was then purified by silica gel column chromatography (hexane:ethyl acetate=4:1 to 1:4 by volume) to obtain 8.45 g (yield: 75.3%) of the above captioned compound as yellowish white crystals.

mp: 122 to 123° C.;
$[\alpha]_D^{24}$: −66.8° (c 1.00, toluene)
$^1$H-NMR(CDCl$_3$)δ: 6.99–8.05(m, ArH)
$^{31}$P-NMR(CDCl$_3$)δ: 29.03
CI-Mass spectrum m/z: 703(M$^+$+H)

Example 14

Synthesis of (S)-2-di(2-naphthyl)phosphino-2'-(trifluoromethanesulfonyloxy)-1,1'-binaphthyl Trichlorosilane (3.7 ml, 37 mmol) was added to a mixture of (S)-2-di(2-naphthyl)phosphinyl-2'-(trifluoromethanesulfonyloxy)-1,1'-binaphthyl (8.59 g, 12.2 mmol), toluene (170 ml) and dimethylaniline (4.6 ml, 36 mmol). The resulting reaction mixture was stirred for 1 hour at 90° C. and thereafter heated at reflux for 22 hours. The reaction mixture was cooled, and 1N NaOH solution (150 ml) was gradually added dropwise to the reaction mixture. The aqueous layer was extracted with toluene (50 ml) and the combined organic layer was washed twice with water (150 ml), 1N hydrochloric acid (150 ml) and water (150 ml) in that order, followed by concentrating the organic layer. The organic solution was then purified by silica gel column chromatography (hexane:ethyl acetate=1:0 to 9:1 by volume) to obtain 7.00 g (yield: 83.9%) of the above captioned compound as a yellow solid.

mp: 113 to 115° C.
$[\alpha]_D^{24}$: +3.9° (c 1.00, EtOH)
$^1$H-NMR(CDCl$_3$)δ: 6.86–8.07(m, ArH)
$^{31}$P-NMR(CDCl$_3$)δ: −10.95
CI-Mass spectrum m/z: 686(M$^+$)

Example 15

Synthesis of (S)-2-di(2-naphthyl)phosphino-2'-di(2-naphthyl)phosphinyl-1,1'-binaphthyl (S)-2-di(2-naphthyl)phosphino-2'-(trifluoromethanesulfonyloxy)-1,1'-binaphthyl (1.00 g, 1.46 mmol), DABCO (0.327 g, 2.91 mmol) and [1,2-bis(diphenylphosphino)ethane] nickel dichloride (76.9 mg, 0.146 mmol) were dissolved in DMF (4 ml), and the solution was stirred for 1 hour at room temperature. The solution was then admixed with di(2-naphthyl)phosphine oxide (530 mg, 1.8 mmol) as a solution in DMF (2.4 ml). Then, the solution was stirred for 16 hours at 100° C. After concentrating and thereafter admixing with methylene chloride (10 ml), the organic solution was washed with water (10 ml) and 1N hydrochloric acid (10 ml). Then, after concentrating, the organic solution was purified by silica gel column chromatography (hexane:ethyl acetate=1:0 to 0:1 by volume) to obtain 0.59 g (yield: 56.2%) of the above captioned compound as a yellowish white solid.

mp: 285 to 287° C.
$[\alpha]_D^{24}$: −51.4° (c 1.08, CHCl$_3$)
$^{31}$P-NMR(CDCl$_3$)δ: −13.05(s), 28.28(s)
CI-Mass spectrum m/z: 840(M$^+$+H)

Example 16

Synthesis of (S)-2,2'-bis(di(2-naphthyl)phosphino)-1,1'-binaphthyl

Trichlorosilane (14.1 ml, 104 mmol) was added to a mixture of (S)-2-di(2-naphthyl)phosphino-2'-di(2-naphthyl)phosphinyl-1,1'-binaphthyl (15.04 g, 17.9 mmol), dimethylaniline (12.55 g, 103 mmol) and toluene (270 ml). The resulting reaction mixture was stirred for 1 hour at 90° C. and thereafter heated at reflux for 28 hours. The reaction mixture was cooled in an ice/water bath, and 20% NaOH solution (120 ml) was added to the reaction mixture. The aqueous layer was extracted with toluene and the organic layer was washed with water (50 ml), 2N hydrochloric acid (10 ml) and water (50 ml) in that order, followed by concentrating. Then, the organic solution was purified by silica gel column chromatography (hexane:ethyl acetate=1:0 to 1:1 by volume) to obtain 14.9 g (yield: 87%) of the above captioned compound as a white solid.

mp: 291 to 293° C. $[\alpha]_D^{24}$: −132.2° (c 0.99, CHCl$_3$)
$^{31}$P-NMR(CDCl$_3$)δ: −13.57(s)
CI-Mass spectrum m/z: 824(M$^+$+H+1)

While the invention has been described in detail and with reference to specific embodiments thereof, it will be apparent to one skilled in the art that various changes and modifications can be made therein without departing from the spirit and scope thereof.

What is claimed is:

1. A method for producing 2,2'-bis(diphenylphosphino)-5,5',6,6',7,7',8,8'-octahydro-1,1'-binaphthyl or 2,2'-bis(diphenylphosphino)-1,1'-binaphthyl derivative represented by general formula (1)

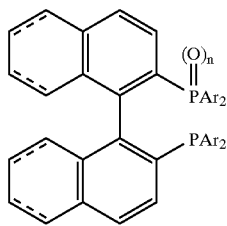

(1)

where n represents 0 or 1; the double line having a continuous line and a dotted line represents a double bond or a single bond such that the ring having the double line forms a naphthalene ring or an octahydronaphthalene ring with an adjacent benzene ring; and Ar represents a phenyl group; a substituted phenyl group having 1 to 3 substituents, which may be the same or different, selected from the group consisting of a halogen atom, a lower alkyl group, a lower alkoxy group and a halogenated lower alkyl group; or a naphthyl group which may have a lower alkyl or a lower alkoxy substituent; comprising (1) reacting 2,2'-bis(trifluoromethanesulfonyloxy)-1,1'-octahydrobinaphthyl represented by general formula (4)

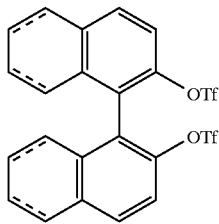

(4)

where the double line having a continuous line and a dotted line represent a double bond or a single bond such that the ring having the double line forms a naphthalene ring or an octahydronaphthalene ring with an adjacent benzene ring; and Tf represents trifluoromethanesulfonyl groups with a phosphine oxide represented by general formula (3)

$Ar_2P(O)H$ (3)

where Ar has the same meaning as defined above in the presence of a first transition metal/phospine complex to prepare 2-trifluoromethanesulfonyloxy-2'-diarylphosphinyl- 1,1'-binaphthyl or 2-trifluoromethanesulfonyloxy-2'diarylphosphinyl- 1,1'-octahydrobinaphthyl represented by general formula (5)

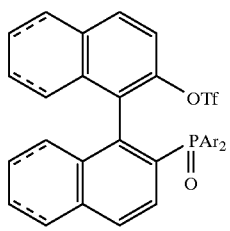

(5)

where the double line having a continuous line and a dotted line, Tf and Ar have the same meanings as defined above and reducing the reaction product; and (2) reacting 2-triiluoromethanesulfonyloxy-2'-diarylphosphino-1,1'-binaphthyl or
2-trifluoromethanesulfonyloxy-2'-diarylphosphino-1,1-octahydrobinaphthyl represented by the general formula (2)

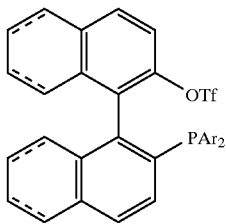

(2)

where Tf represents trifluoromethanesulfonyl group; and the double line having a continuous line and a dotted line, and Ar have the same meanings as defined above with a phosphine oxide represented by general formula (3)

$Ar_2P(O)H$ (3)

where Ar has the same meaning as defined above in the presence of a second transition metal/phosphine complex other than said first metal/phosphine complex, and reducing the reaction product when n is 1 to obtain compounds of the formula (1) where n is 0.

* * * * *